United States Patent [19]
Ono

[11] Patent Number: 5,132,441
[45] Date of Patent: Jul. 21, 1992

[54] AMINO ACID DERIVATIVES

[75] Inventor: Mitsunori Ono, Kanagawa, Japan

[73] Assignee: Fuji Photo Film Co., Ltd., Kanagawa, Japan

[21] Appl. No.: 466,904

[22] Filed: Jan. 18, 1990

[30] Foreign Application Priority Data

Jan. 18, 1989 [JP] Japan .................................. 1-9503

[51] Int. Cl.$^5$ ............................................ C08H 3/00
[52] U.S. Cl. ............................... 554/36; 558/234; 560/155; 554/42; 554/51; 554/106
[58] Field of Search .................. 260/404.5 A, 399, 404, 260/408; 558/234; 560/155

[56] References Cited

PUBLICATIONS

Chemical Abstract, vol. 112, p. 775, 1990, Abstract of EP 321,296, Kamata et al.
Cover p. of EP 321,296, p. 55 of EP 321,296.
Chemical Abstracts vol. 112, #21.

*Primary Examiner*—Jose G. Dees
*Assistant Examiner*—Deborah D. Carr
*Attorney, Agent, or Firm*—Sughrue, Mion, Zinn, Macpeak & Seas

[57] ABSTRACT

Disclosed is an amino acid derivative represented by the general Formula (I):

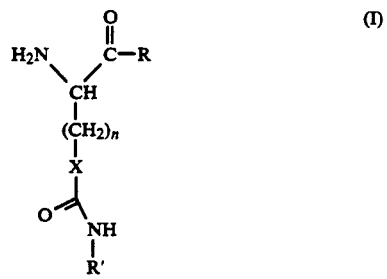

wherein R is a group whose conjugate acid has a pKa ranging from 10 to 16, R' is a straight chain alkyl group having 12 to 20 carbon atoms, n is an integer of 0 to 4, and X is —O—, —NH— or —S—. These amino acid derivatives each having various eliminative groups can be synthesized by simple steps using optically active amino acids.

5 Claims, 6 Drawing Sheets

AMINO ACID DERIVATIVES

FIELD OF THE INVENTION

The present invention relates to amino acid derivatives useful for forming a polymeric monomolecular film.

BACKGROUND OF THE INVENTION

Polymeric monomolecular films are widely applicable as functional films as sensors and as transmission control films for material delivery because of their selective permeability to gas molecules or ions. In addition, such films are useful materials for electronic devices and for surface protection due to their thinness and tightness.

Amino esters having long chain alkyl groups have been considered preferable for the production of monomolecular films composed of amino acid derivatives.

Prior-art methods for forming monomolecular films by polymerization, such as photopolymerization, group polymerization, and the like, are described in detail in J. Org. Synth. Chem. Soc., vol. 40, p.377 (1982).

However, there are very few compounds wherein polymerization occurs spontaneously only when their molecules are oriented in the monomolecular film matrixes.

As amino esters which have a long chain alkyl group and wherein the polymerization occurs spontaneously, methyl-2-aminooctadecanoate and methyl-2-aminohexacosanoate are disclosed in Ringsdorf, Macromol. Chem., Rapid Commun., vol. 3, pp. 167-174 (1982).

The problems with these amino esters are that they are complicated to synthesize, that only the racemic modifications are produced, that the eliminative groups (groups removed from the molecule upon spontaneous polymerization) are limited to low reactive group ($-O-CH_3$) so that the polymerization takes several days at room temperature.

Accordingly, the compounds to overcome the above problems have been desired.

SUMMARY OF THE INVENTION

It is therefore one object of the present invention to provide amino acid derivatives having various eliminative groups which can be synthesized by simple steps using optically active amino acids.

Other objects of the present invention will appear in the following description.

These and other objects on the invention are provided by an amino acid derivative represented by the general Formula (I):

$$\begin{array}{c} \text{H}_2\text{N} \diagdown \quad \overset{\overset{\displaystyle O}{\|}}{\text{C}}-\text{R} \\ \diagup\text{CH} \\ |\\ (\text{CH}_2)_n \\ | \\ \text{X} \\ | \\ \text{O} \diagup \\ \quad\quad\diagdown \text{NH} \\ \quad\quad\quad | \\ \quad\quad\quad \text{R}' \end{array} \quad (\text{I})$$

wherein R is a group whose conjugate acid (RH wherein H represents a hydrogen atom) has a pKa ranging from 10 to 16, R' is a straight chain alkyl group having 12 to 20 carbon atoms, n is an integer of 0 to 4, and X is $-O-$, $-NH-$ or $-S-$. The group represented by R functions as an eliminative group upon polymerization for forming monomolecular films.

DETAILED DESCRIPTION OF THE INVENTION

Figure 1:
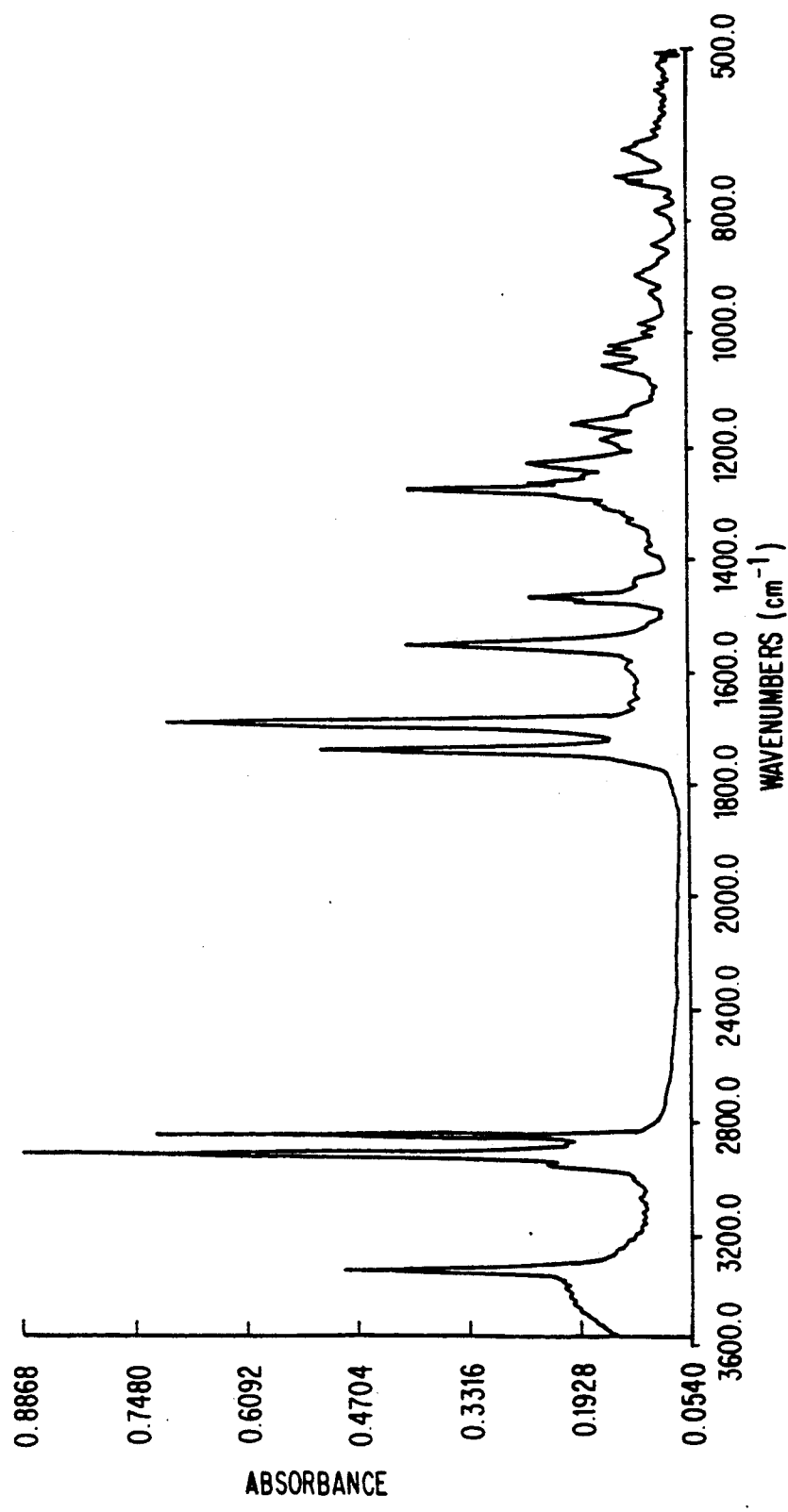
FIG. 1 is a graph showing the IR spectrum of Compound (1) in Example 1.

In Formula (I), R is preferably a methoxy group, a phenoxy group, a dichloroethoxy group, a trichloroethoxy group, a monochloroethoxy group, an imidazolyl group and a $$CH_3-\overset{\overset{\displaystyle O}{\|}}{C}-\overset{\overset{\displaystyle CH_3}{|}}{N}-O-$$

In particular, a phenoxy group, a dichloroethoxy group and a $$CH_3-\overset{\overset{\displaystyle O}{\|}}{C}-\overset{\overset{\displaystyle CH_3}{|}}{N}-O-$$

group are preferable.

R' is a straight chain alkyl group having 12 to 20 carbon atoms, preferably a dodecyl group, a hexadecyl group or an octadecyl group. An octadecyl group is particularly preferable.

n is an integer of 0 to 4, preferably 1 to 4, more preferably 1 or 2. X is $-O-$, $-NH-$ or $-S-$.

There is hereinafter shown a general, non-limiting example of the steps for synthesizing the amino ester derivatives of the present invention.

First, the amino group of an amino methyl ester represented by the general Formula (II) is protected with a t-butoxycarbonyl group (hereinafter referred to as Boc) to obtain a Boc-amino methyl ester (represented by the general Formula (III), wherein R is $-O-CH_3$).

$$\begin{array}{cc} \text{H}_2\text{N}\diagdown \quad \overset{\overset{\displaystyle O}{\|}}{\text{C}}-\text{OCH}_3 & \overset{\text{H}}{\text{Boc.N}}\diagdown \quad \overset{\overset{\displaystyle O}{\|}}{\text{C}}-\text{R} \\ \diagup & \diagup \\ | & | \\ (\text{CH}_2)_n & (\text{CH}_2)_n \\ | & | \\ \text{XH} & \text{XH} \\ (\text{II}) & (\text{III}) \end{array}$$

Then, the amino group of the Boc-amino methyl ester (represented by Formula (III), wherein R is $-O-CH_3$) is protected with a tetrahydropyranyl group (hereinafter referred to as THP). The resulting ester is hydrolyzed by alkali, and subsequently esterified with various alcohols (ROH, wherein R corresponds to R in the general Formula (I) and (III)) using carbonyldiimidazole, followed by elimination of the THP protective group with paratoluenesulfonic acid (hereinafter referred to as PTS). Thus, the Boc-amino esters of various alcohols (Formula (III)) are obtained.

The Boc-amino esters (Formula (III)) are reacted with carbonyl chloride produced from trichloromethyl chloroformate (hereinafter referred to as TCF), and then reacted with amines represented by the general formula R'—NH₂, thereby obtaining various Boc-amino esters represented by the general Formula (IV):

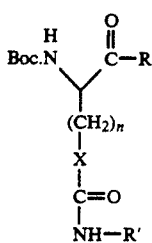

For the Boc-amino esters represented by Formula (IV), the Boc protective group is eliminated with trifluoroacetic acid (hereinafter referred to as TFA), and subsequently treated with a saturated aqueous solution of NaHCO₃. Thus, the various amino esters represented by Formula (I) are obtained.

Examples of the preferred compounds of the present invention include but are not limited to the following:

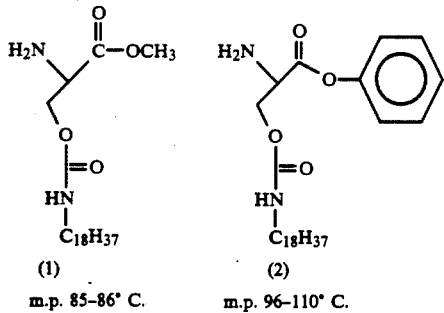

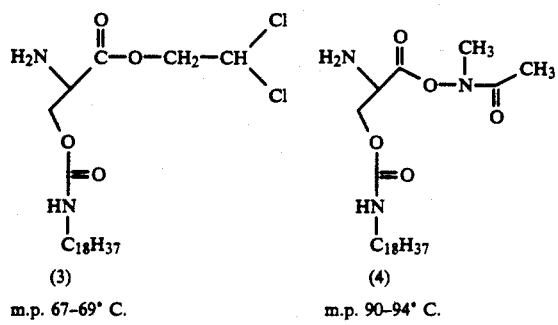

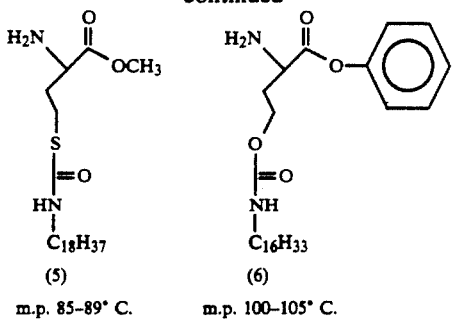

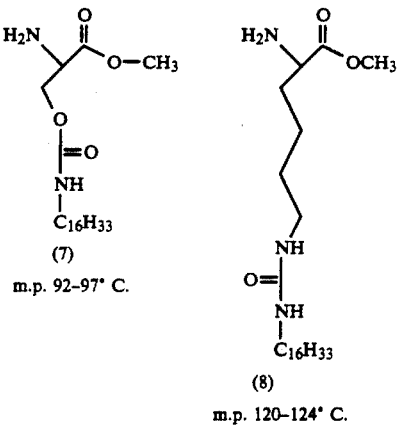

The amino acid derivatives each having various eliminative groups in the present invention can be synthesized by simple steps using optically active amino acids described above.

The compounds of the present invention are spontaneously polymerized in monomolecular film matrixes at high reaction rate because they have linking groups represented by —X—CO—NH— and reactive eliminative groups, and therefore are useful for the formation of the monomolecular films and built-up films of polyamino acids. The resulting polymeric monomolecular films are superior in selective permeability.

The invention will now be illustrated by reference to non-limiting examples. Unless otherwise indicated, all percents, ratios, parts, etc., are by weight.

EXAMPLE 1

Synthesis of Compound (1) Represented by Formula (I) Wherein R is —O—CH₃, R' is —C₁₈H₃₇, X is O and n is 1

In 50 ml of methanol, 2.0 g (30 millimoles) of KOH (85% content) was dissolved and 4.7 g (30 millimoles) of e-serine methyl ester hydrochloride was added thereto. The mixture was stirred for 40 minutes. Thereto was added 3.0 g (30 millimoles) of triethylamine, and then 6.6 g (30 millimoles) of (Boc)₂O in a THF solution was added dropwise. The resulting mixture was allowed to stand overnight, and then the methanol and the THF were distilled away under reduced pressure. After adding ethyl acetate to the residue, an organic layer was washed with water, followed by Na₂SO₄ drying. Then, the ethyl acetate was distilled away under reduced pressure. The residue was purified by SiO₂ column chromatography (eluent: hexane/ethyl acetate=8/2). Thus, 5.6 g (24 millimoles, yield 80%) of the compound represented by Formula (III) wherein R is —O—CH₃, n is 1 and X is O was obtained as a colorless liquid.

Then, 1.8 g (9.1 millimoles) of TCF was added dropwise to 300 mg of active carbon to produce phosgene, which was introduced into 50 ml of CH₂Cl₂ in a three-neck flask under ice cooling. Subsequently, there was added dropwise thereto under ice cooling a mixture solution of 2.0 g (14 millimoles) of the previously obtained amino methyl ester (represented by Formula (III) wherein R is —O—CH₃, n is 1 and X is O) and 0.92 g (9.1 millimoles) of triethylamine in 30 ml of CH₂Cl₂. After expelling the phosgene remaining in the system by blowing nitrogen therethrough, there was added dropwise thereto a mixture solution of 2.5 g (9.1 millimoles) of stearylamine and 0.92 g (9.1 millimoles) of triethylamine in CH₂Cl₂. After stirring for 1 hour, the resulting mixture was allowed to stand for 2 days. The reaction was terminated by adding water. Then, an organic layer was washed with water 3 times, followed by Na₂SO₄ drying. The CH₂Cl₂ was distilled away under reduced pressure. The residue was purified by silica gel chromatography (eluent: hexane/ethyl acetate=7/3). Thus, 2.5 g (5.1 millimoles, yield 56%) of a Boc-amino ester (represented by Formula (IV) wherein R is —O—CH₃, n is 1, X is O and R' is —C₁₈H₃₇ was obtained as a colorless solid (m.p. 96°-98° C.; ¹H·NMR(CDCl₃,δ) 0.88 (hydrocarbon chain-CH₃, 3H, t), 1.08-1.40 (hydrocarbon chain-CH₂-, 32H), 1.45 (—CO—O—C(CH₃)₃, 9H), 3.13 (amide-CH₂-hydrocarbon chain, 2H), 3.75 (—CO—O—CH₃, 3H), 4.24-4.60 (serine CH, serine CH₂, 3H)).

Subsequently, 0.50 g (1.0 millimole) of the Boc-amino ester (represented by Formula (IV) wherein R is —O—CH₃, n is 1, X is O and R' is —C₁₈H₃₇) was dissolved in 3 ml of CH₂Cl₂. 3 ml of TFA was added thereto, followed by stirring for 30 minutes. Then, the solvent of the resulting solution was distilled away under reduced pressure under ice cooling. After 3 ml of CH₂Cl₂ was added to the residue, the CH₂Cl₂ was distilled away under reduced pressure again, followed by drying under reduced pressure under dry ice-acetone cooling. Thus, a colorless solid was obtained.

Figure 2:
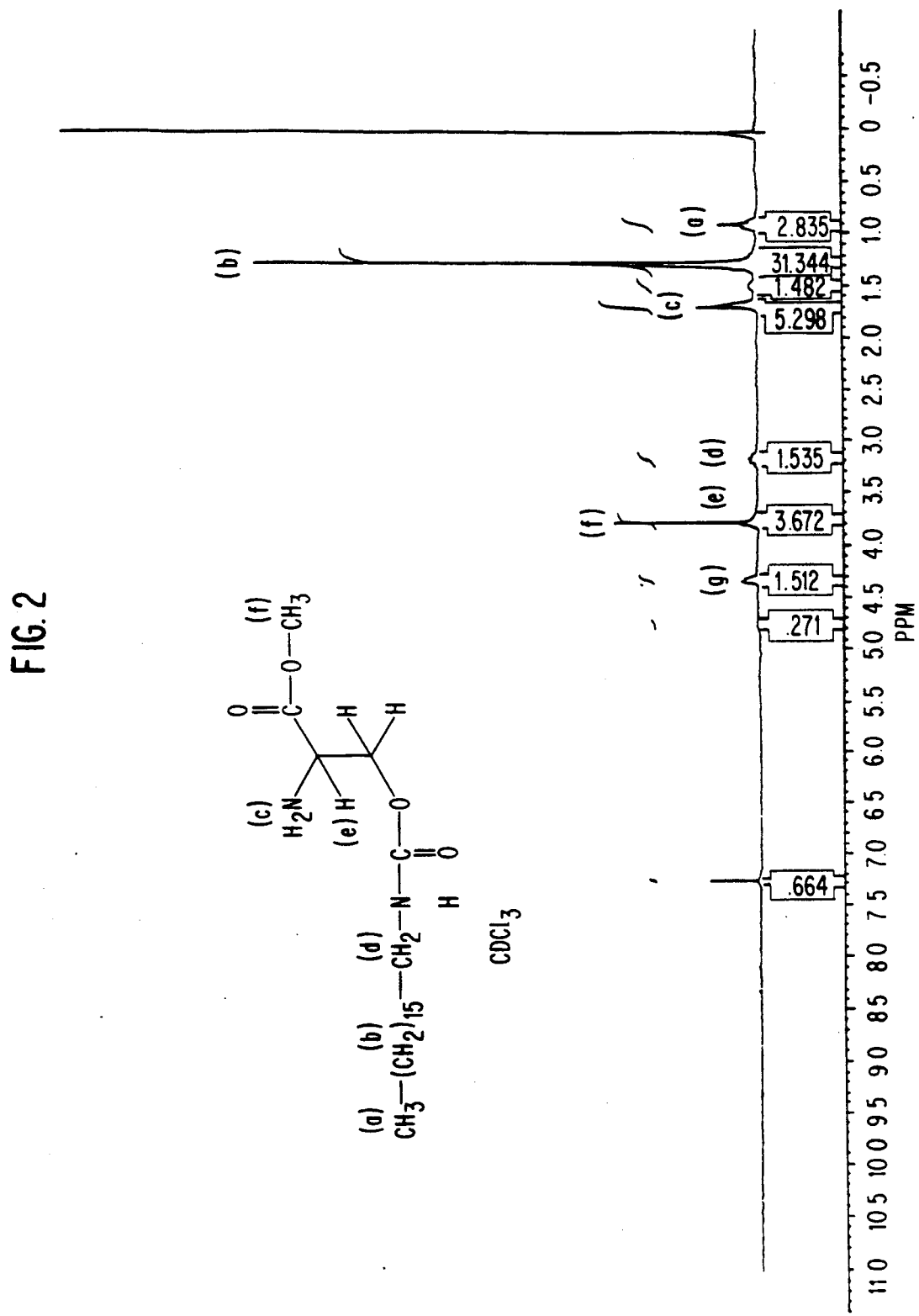
FIG. 2 is a graph showing the NMR spectrum of Compound (1) in Example 1.

Then, 0.5 g of this colorless solid was dissolved in CH₂Cl₂, and a saturated aqueous solution of NaHCO₃ was added thereto. The organic layer was washed with water, followed by Na₂SO₄ drying. The CH₂Cl₂ was distilled away under reduced pressure. Thus, 0.34 g of an amino ester (represented by Formula (I) wherein R is —O—CH₃, n is 1, X is O and R' is —C₁₈H₃₇, namely Compound (1)) was obtained m.p. 85°-86° C.; IR and ¹H-NMR spectra are shown in FIGS. 1 and 2, respectively).

EXAMPLE 2

Synthesis of Compound (2) Represented by Formula (I) Wherein R is

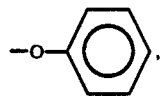

R' is —C₁₈H₃₇, X is O and n is 1

A solution of 200 mg (110 millimoles) of PTS in 2 ml of THF was added dropwise to a mixture solution of 21 g (96 millimoles) of an amino methyl ester (represented by Formula (III) wherein R is —O—CH₃, n is 1 and X is O) and 40 g (480 millimoles) of DHP in 450 ml of CHCl₃, followed by stirring for 3 hours. The DHP and the CHCl₃ were distilled away under reduced pressure, and thereafter CHCl₃ was added thereto, followed by washing with an aqueous solution of NaHCO₃, water washing and Na₂SO₄ drying. Then, the CHCl₃ was distilled away under reduced pressure to obtain a colorless solid. This reaction product was dissolved in 500 ml of methanol, and a solution of 4.5 g (100 millimoles) of 93% NaOH in 80 ml of water was added thereto. The mixture was allowed to stand overnight. After the solvent was distilled away, water was added thereto and the aqueous layer was washed with ethyl acetate. Thereafter, ethyl acetate was added thereto again. The aqueous layer was acidified (pH about 3) with dilute hydrochloric acid, and then extracted with ethyl acetate, followed by water washing and Na₂SO₄ drying. The ethyl acetate was thereafter distilled away under reduced pressure, and thus 21 g (73 millimoles) of a carboxylic acid was obtained as a highly viscous liquid.

A mixture solution of 2.80 g (9.7 millimoles) of this carboxylic acid and 1.57 g (9.7 millimoles) of carbonyldiimidazole in 70 ml of THF was stirred for 1 hour, and a solution of 0.91 g (9.7 millimoles) of phenol in 30 ml of THF was added thereto. The resulting solution was stirred at room temperature for 1 hour and under reflux for 1.5 hours, and then allowed to stand overnight. The solvent was thereafter distilled away under reduced pressure. Ethyl acetate was added to the residue, which was washed with water 3 times, followed by Na₂SO₄ drying. The solvent was distilled away under reduced pressure. The residue was purified by silica gel chromatography (eluent: hexane/ethyl acetate=9/1) to obtain 1.37 g of a colorless solid.

950 mg (5 millimoles) of PTS was added to a mixture solution of 5.5 g (15 millimoles) of the above-mentioned solid, 200 ml of methanol and 20 ml of water, followed by stirring at room temperature for 2 hours.

Then, 950 mg (5 millimoles) of PTS was added thereto, and stirring was further continued for 2 hours. The solvent was thereafter distilled away under reduced pressure. The residue was purified by silica gel chromatography (eluent: hexane/ethyl acetate=7/3). Thus, 1.2 g of a Boc-amino ester (represented by Formula (III) wherein R is

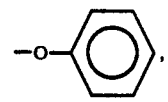

n is 1 and X is O ) was obtained as a colorless solid.

Phosgene generated from 1.2 g (6.0 millimoles) of TCF and 300 mg of active carbon was blown through 50 ml of CH₂Cl₂ under ice cooling. Then, there was added dropwise thereto under ice cooling (for 30 minutes) a mixture solution of 1.18 g (4.2 millimoles) of the Boc-amino ester (represented by Formula (III) wherein R is

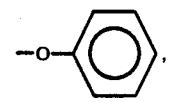

n is 1 and X is O) and 0.42 g (4.2 millimoles) of triethylamine in 25 ml of CH₂Cl₂. After stirring for 3 hours, the phosgene was expelled by blowing nitrogen therethrough, and there was added thereto a mixture solution of 1.14 g (4.2 millimoles) of stearylamine and 0.42 g (4.2 millimoles) of triethylamine in 50 ml of $CH_2Cl_2$.

After the resulting mixture was allowed to stand overnight, an organic layer was washed by the addition of water, followed by $Na_2SO_4$ drying. The solvent was distilled away under reduced pressure. The residue was purified by silica gel chromatography (eluent: hexane/ethyl acetate=8/2) to obtain 1.18 g of a colorless solid. 400 mg of this was recrystallized from ethyl acetate. As a result, there was obtained 0.32 g of a Boc-amino ester (represented by Formula (IV) wherein R is

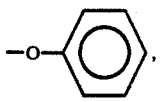

n is 1, X is O and R' is —$C_{18}H_{37}$)(m.p. 97.0°–98.0° C.; $^1$H-NMR(CDCl$_3$,δ) 0.85 (hydrocarbon chain-CH$_3$, 3H,), 1.00–1.40 (hydrocarbon chain-CH$_2$-, 32H), 1.46 (—CO—O—C(CH$_3$)$_3$, 9H), 3.15 (amide-CH$_2$-hydrocarbon chain, 2H), 4.35–4.86 (serine CH$_2$, CH, 3H), 7.05–7.45

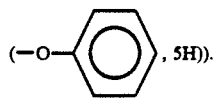

200 mg (0.35 millimole) of the Boc-amino ester (represented by Formula (IV) wherein R is

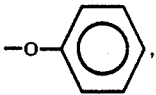

n is 1, X is O and R' is —$C_{18}H_{37}$) was dissolved in a solution of 4 ml of TFA in 4 ml of $CH_2Cl_2$, followed by stirring for 30 minutes. Then, the solvent was distilled away under reduced pressure. It was further repeated twice that $CH_2CL_2$ was added to the residue and distilled away under reduced pressure, followed by drying under reduced pressure. Thus, a colorless solid was obtained. 100 mg (0.17 millimole) of this was dissolved in CHCl$_3$ and treated with a saturated aqueous solution of NaHCO$_3$. An organic layer was dried over Na$_2$SO$_4$, and the solvent was distilled away under reduced pressure. Thus, 60 mg (0.13 millimole) of an amino ester (represented by Formula (I) wherein R is

Figure 3:
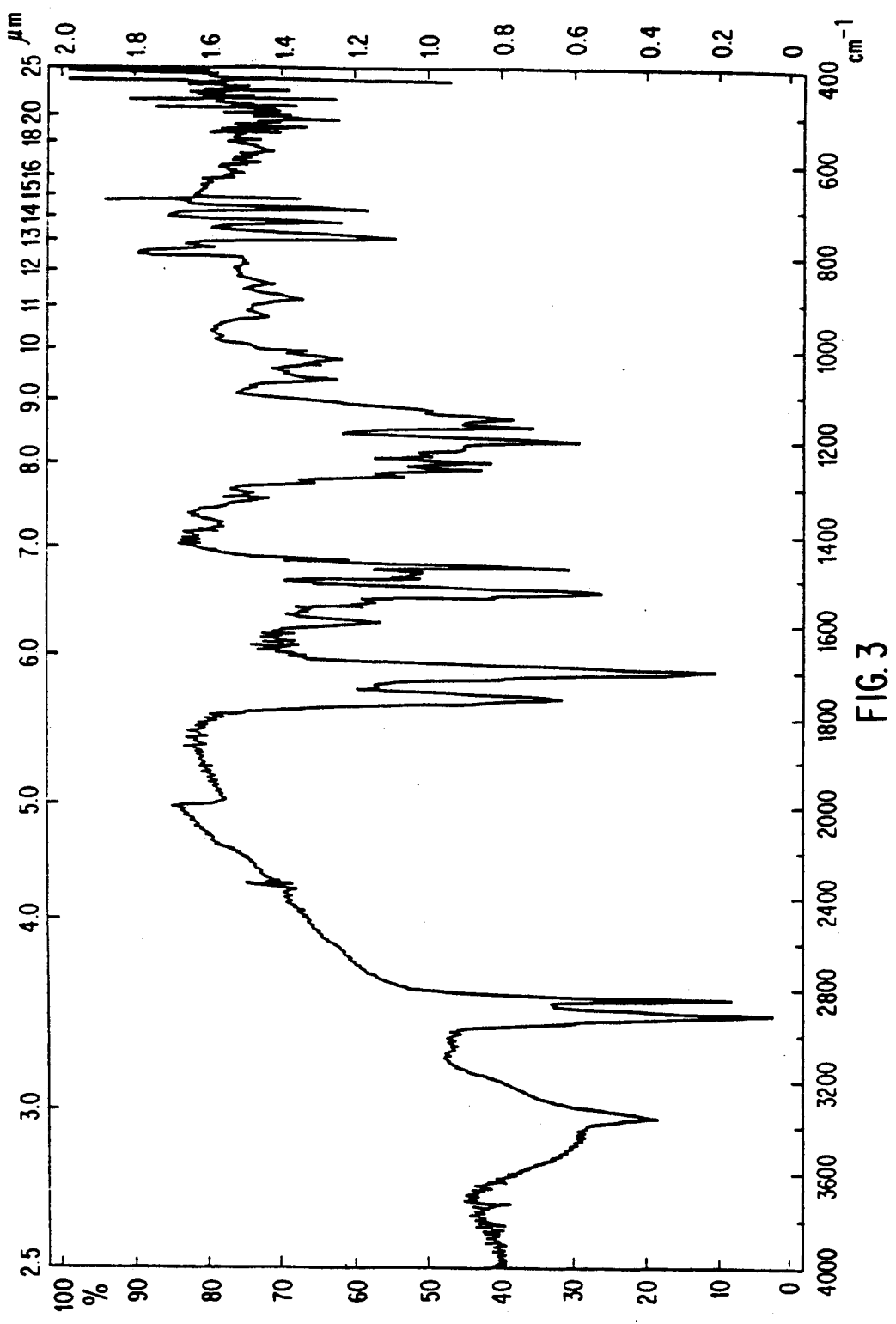
FIG. 3 is a graph showing the IR spectrum of Compound (2) in Example 2.
Figure 4:
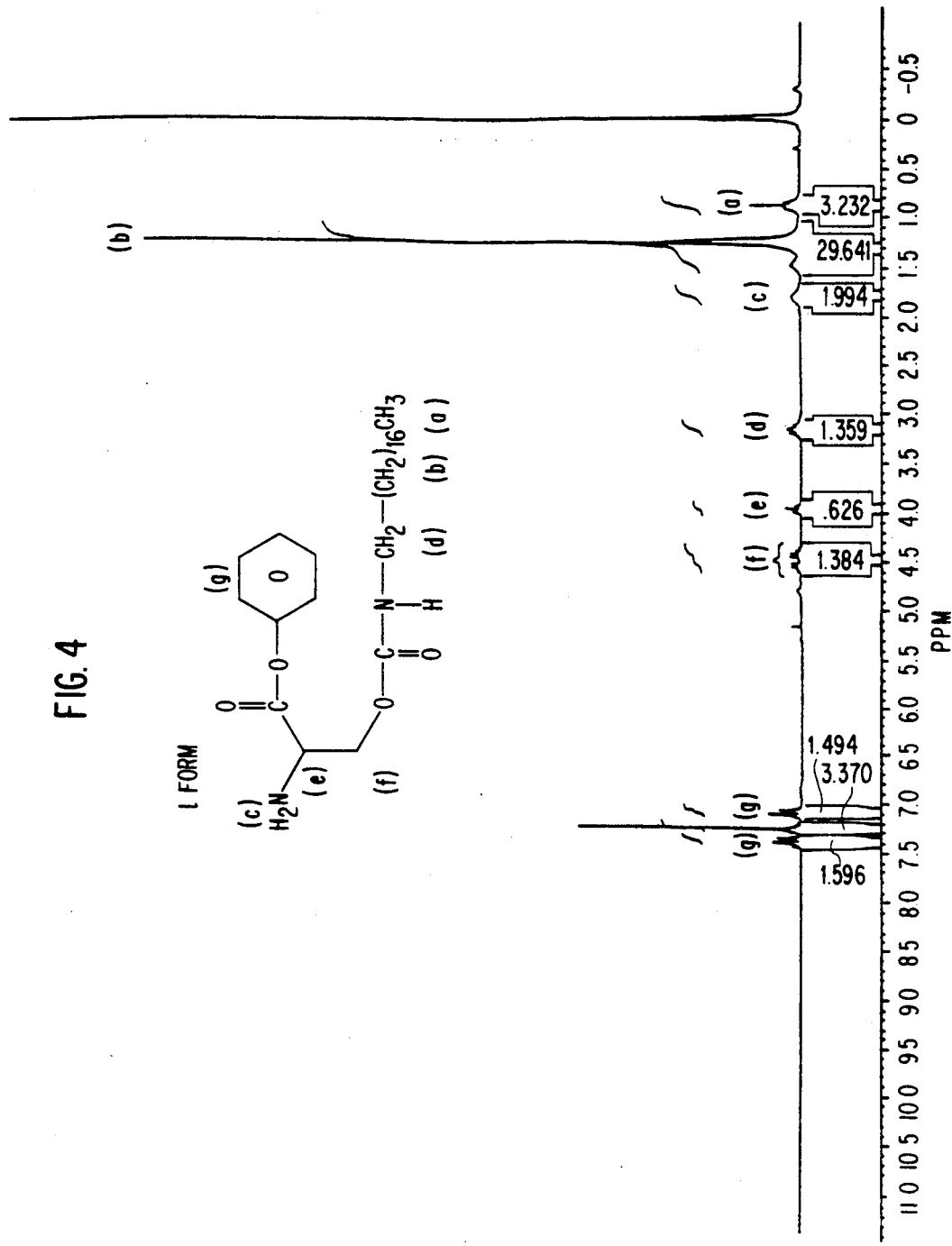
FIG. 4 is a graph showing the NMR spectrum of Compound (2) in Example 2.

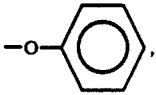

n is 1, X is O and R' is —$C_{18}H_{37}$, namely Compound (2)) was obtained (m.p. 96°–110° C. (decomposed); the IR and $^1$H-NMR spectra are shown in FIGS. 3 and 4, respectively).

EXAMPLE 3

Synthesis of Compound (3) Represented by Formula (I) Wherein R is —O—CH$_2$CHCl$_2$, R' is —$C_{18}H_{37}$, n is 1 and X is O A mixture solution of 11.3 g (39 millimoles) of the serine derivative from Example 2, whose amino group was protected with Boc and whose hydroxyl group was protected with THP, and 7.6 g (47 millimoles) of carbonyldiimidazole in 300 ml of THF was stirred for 1 hour, and then a solution of 4.5 g (39 millimoles) of dichloroethanol in 5 ml of THF was added dropwise thereto. The resulting solution was allowed to stand overnight. The solvent was thereafter distilled away under reduced pressure. Then, ethyl acetate was added to the residue, followed by brine washing and Na$_2$SO$_4$ drying. The ethyl acetate was distilled away under reduced pressure. The residue was purified by silica gel chromatography (eluent: hexane/ethyl acetate=8/2) to obtain 11.2 g (29 millimoles, yield 74%) of a colorless liquid.

A solution of 300 mg (1.6 millimoles) of PTS in 25 ml of water was added to a solution of 1.9 g (4.9 millimoles) of above-mentioned liquid in 100 ml of methanol, followed by stirring for 2 hours. Thereafter, 300 mg (1.6 millimoles) of PTS was added thereto and the reaction was conducted for 4 hours. In this case, the pH of the reaction solution was adjusted to about 3. Then, a part of the solvent was distilled away under reduced pressure, and ethyl acetate and water were added to the residue to extract an organic layer. The organic layer was washed with water to pH 7, followed by Na$_2$SO$_4$ drying. After the solvent was distilled away under reduced pressure, the residue was purified by silica gel chromatography (eluent: hexane/ethyl acetate=7/3). Thus, 0.94 g (3.1 millimoles, yield 63%) of a Boc-amino ester (represented by Formula (III) wherein R is —O—CH$_2$CHCl$_2$, n is 1 and X is O ) was obtained.

Phosgene generated from 2.1 g (10.6 millimoles) of TCF and 400 mg of active carbon was blown through 50 ml of CH$_2$Cl$_2$ under ice cooling. Then, there was added dropwise thereto a solution of 1.14 g (3.8 millimoles) of the Boc-amino ester (represented by Formula (III) wherein R is —O—CH$_2$CHCl$_2$, n is 1 and X is O) and 0.38 g (3.8 millimoles) of triethylamine in 25 ml of CH$_2$Cl$_2$, followed by stirring for 1 hour. The phosgene was expelled by blowing nitrogen therethrough, and there was added dropwise thereto a solution of 1.02 g (3.8 millimoles) of stearylamine and 0.38 g (3.8 millimoles) of triethylamine in 50 ml of CH$_2$Cl$_2$.

Figure 5:
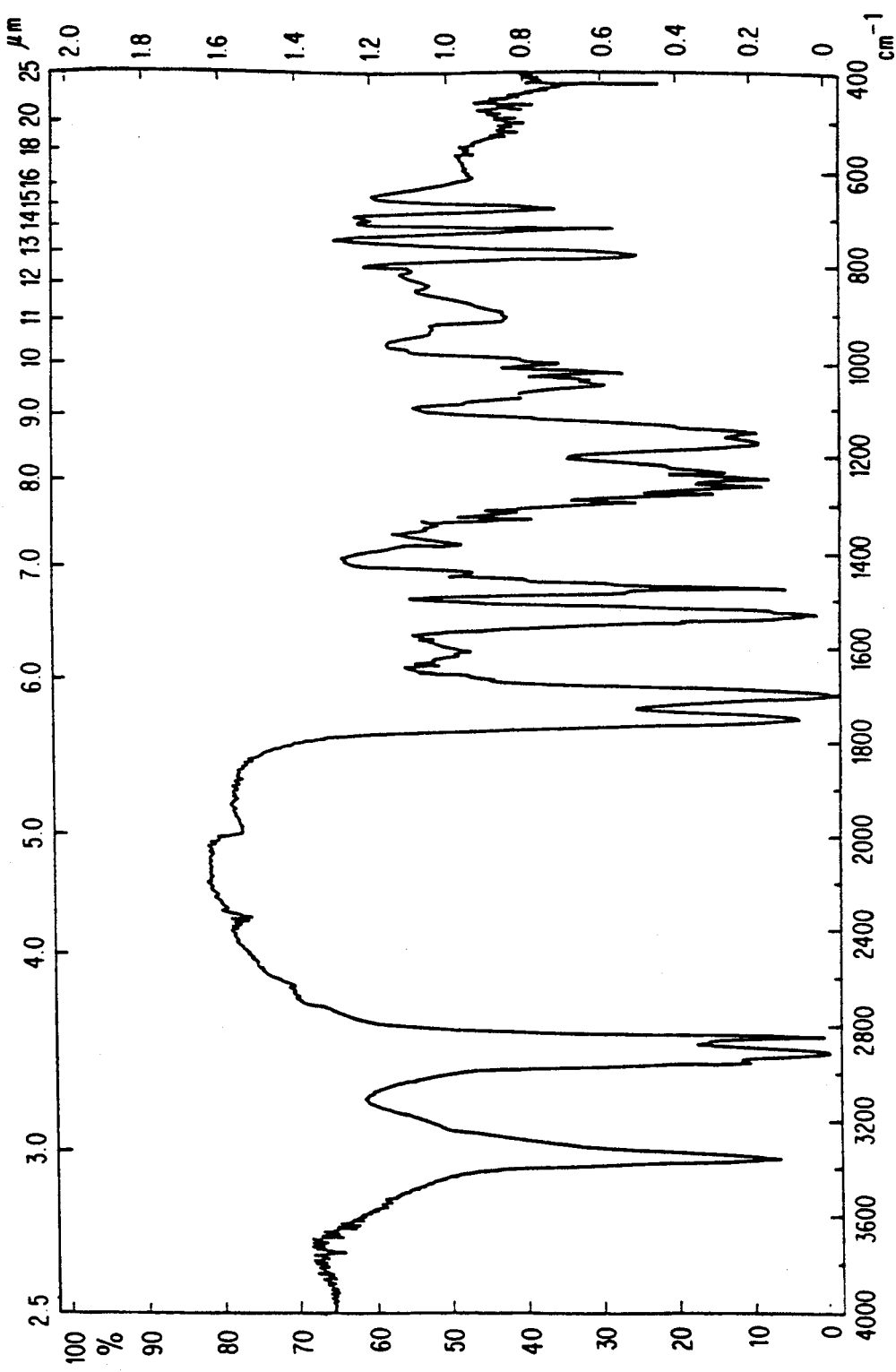
FIG. 5 is a graph showing the IR spectrum of Compound (3) in Example 3.
Figure 6:
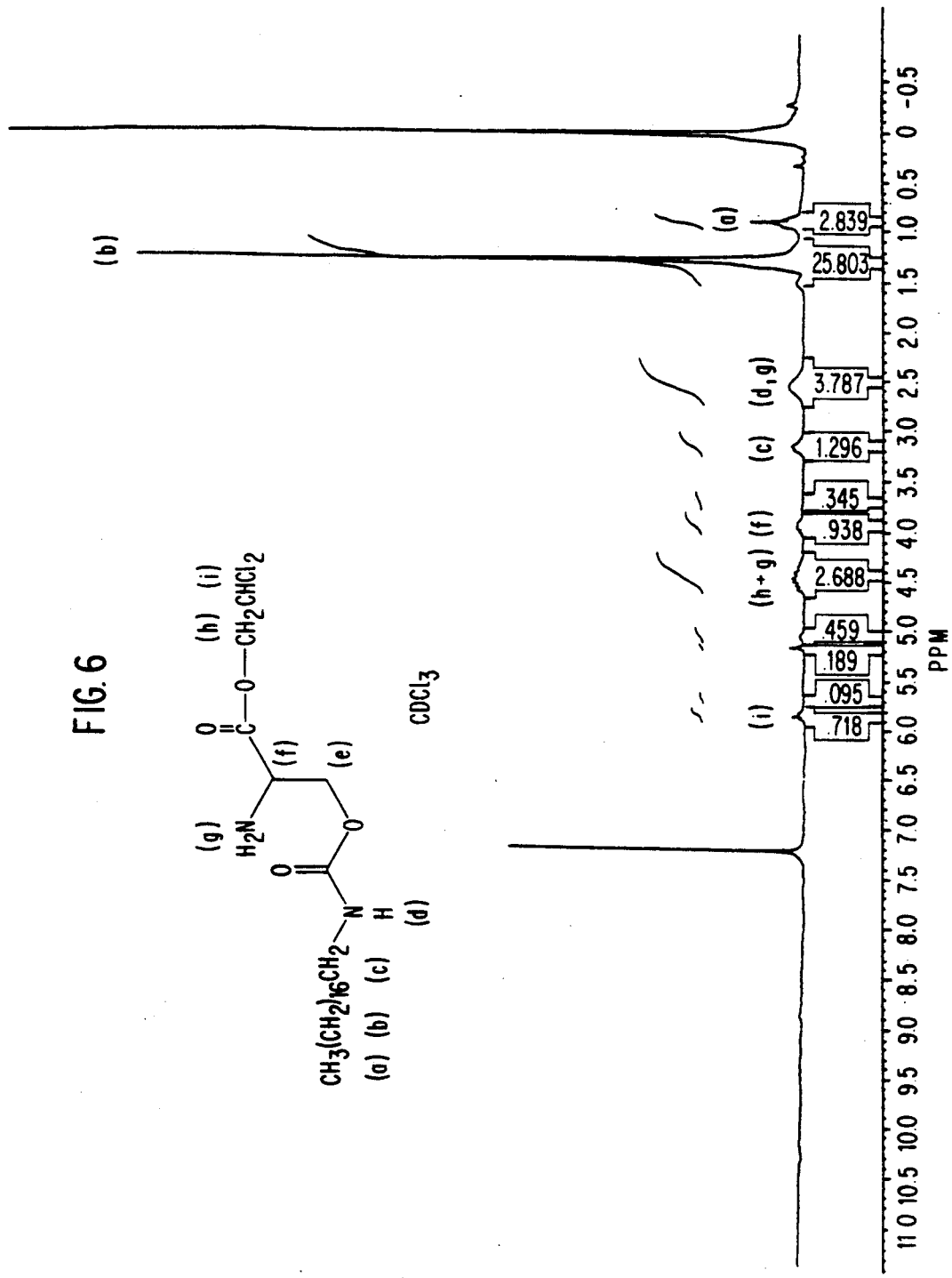
FIG. 6 is a graph showing the NMR spectrum of Compound (3) in Example 3.

After the resulting mixture was allowed to stand overnight, the reaction was terminated by the addition of water. Then, an organic layer was washed with water 3 times, followed by Na$_2$SO$_4$ drying. The CH$_2$Cl$_2$ was distilled away under reduced pressure. The residue was purified by silica gel chromatography (eluent: hexane/ethyl acetate=8/2). As a result, there was obtained 0.51 g (0.86 millimole, yield 23%) of a Boc-amino ester (represented by Formula (IV) wherein R is —O—CH$_2$CHCl$_2$, n is 1, X is O and R' is —$C_{18}H_{37}$)(m.p. 66.0°–68.0° C.; $^1$H-NMR(CDCl$^3$,δ) 0.90 (hydrocarbon chain-CH$_3$, 3H,), 1.10–1.45 (hydrocarbon chain-CH$_2$-, 32H), 1.48 (—CO—O—C(CH$_3$)$_3$, 9H), 3.15 (amide-CH$_2$-hydrocarbon chain, 2H), 4.30–4.80 (dichloroethyl-CH$_2$-, serine CH$_2$, CH, 5H), 5.35(dichloroethyl-CHCL$_2$, 1H)), In a flask, 100 mg of the Boc-amino ester (represented by Formula (IV) wherein R is —O—CH$_2$CHCl$_2$, n is 1, X is O and R' is —C$_{18}$H$_{37}$) was dissolved in 4 ml of CH$_2$Cl$_2$, and 4 ml of TFA was added thereto, followed by the reaction for 30 minutes. Then, the solvent was distilled away under reduced pressure under ice cooling. The residue was dried under reduced pressure. Thus, 60 mg of a colorless solid was obtained. A part of this was treated with a saturated aqueous solution of NaHCO$_3$. Thus, an amino ester (represented by Formula (I) wherein R is —O—CH$_2$CHCl$_2$, n is 1, X is O and R' is —C$_{18}$H$_{37}$, namely Compound (3)) was obtained as a colorless solid (m.p. 67.0°–69.0° C.; IR and $^1$H-NMR spectra are shown in FIGS. 5 and 6, respectively).

EXAMPLE 4

Synthesis of Compound (5) Represented by Formula (I) Wherein R is —O—CH$_3$, R' is —C$_{18}$H$_{37}$, X is —S— and n is 2

2.7 g (20 millimoles) of dl-homocysteine was dissolved in 20 ml of an aqueous solution of 1M NaOH. 5.7 g (45 millimoles) of dimethylphosphinothinol chloride was added dropwise thereto under ice cooling. After stirring for 30 minutes the pH of the resulting solution was adjusted to about 9 by adding an aqueous solution of 0.1M NaOH, and then the aqueous layer was washed with ethyl acetate. The pH of the aqueous layer was adjusted to about 3 by adding an aqueous solution of citric acid, and then the organic layer was extracted with ethyl acetate. The organic layer was washed with water, followed by drying over Na$_2$SO$_4$. The ethyl acetate was thereafter distilled away under reduced pressure. Thus, 3.8 g of colorless liquid was obtained.

3.8 g of the colorless liquid was added to 150 ml of THF and thereto were added 3.1 g (15 millimoles) of dicyclohexylcarbodiimide and 50 ml of methanol. After stirring for 5 hours, the resulting solution was filtered and THF of the filtrate was distilled away under reduced pressure. Ethyl acetate was added thereto. The organic layer was washed with water and 2M HCl was added thereto. The mixture was stirred for 4 hours, and then the solvent was distilled away under reduced pressure. 150 ml of methanol and 0.7 g (15 millimoles) of NaOH (85% content) were added to the residue and a mixture solution of 3.3 g (15 millimoles) of Boc$_2$O and 1.5 g (15 millimoles) of triethylamine in 50 ml of THF was added dropwise thereto. The resulting mixture was allowed to stand overnight. THF was thereafter distilled away under reduced pressure. After adding ethyl acetate to the residue, an organic layer was washed with water, followed by Na$_2$SO$_4$ drying. Ethyl acetate was thereafter distilled away under reduced pressure. 60 ml of THF, 30 ml of H$_2$O and 1.2 g (15 millimoles) of pyridine were added to the residue, and then 30 ml of an aqueous solution of 1M silver nitrate was added dropwise thereto under ice cooling. The mixture was stirred for 1 hour. Subsequently, THF was distilled away and the organic layer was extracted with ethyl acetate. The organic layer extracted was washed with water, followed by Na$_2$SO$_4$ drying. Ethyl acetate was thereafter distilled away. The residue was purified silica gel column chromatography (eluent: hexane/ethyl acetate=6/4). Thus, 1.6 g (6.8 millimoles, yield 45%) of a Boc-amino ester represented by Formula (III) wherein R is —O—CH$_3$, n is 2 and X is —S— was obtained.

Then, 2.0 g (10.2 millimoles) of TCF was added dropwise to 1 g of active carbon to produce phosgene, which was introduced into 100 ml of CH$_2$Cl$_2$ in a three-neck flask under ice cooling. Subsequently, there was added dropwise thereto under ice cooling a mixture solution of 1.2 g (5 milimoles) of the previously obtained Boc-amino ester (represented by Formula (III) wherein R is —O—CH$_3$, n is 2, X is —S—) and 0.50 g (5 millimoles) of triethylamine in 50 ml of CH$_2$Cl$_2$. After expelling the phosgene remaining in the system by blowing nitrogen therethrough, there was added dropwise thereto a mixture solution of 1.35 g (5 millimoles) of stearylamine and 0.50 g (5 millimoles) of triethylamine in 150 ml of CH$_2$Cl$_2$. After the resulting mixture was allowed to stand overnight, the reaction was terminated by adding water. Then, an organic layer was washed with water, followed by Na$_2$SO$_4$ drying. The CH$_2$Cl$_2$ was distilled away under reduced pressure. The residue was purified by silica gel chromatography (eluent: hexane/ethyl acetate=7/3). Thus, 1.30 g (2.4 millimoles, yield 48%) of a Boc-amino ester (represented by Formula (IV) wherein R is —O—CH$_3$, R' is —CH$_{18}$H$_{37}$, n is 2, X is —S—) was obtained. (m.p. 97°–101° C.; $^1$H-NMR (CDCl$_3$, δ) 0.90 (hydrocarbon chain-CH$_3$, 3H), 1.10–1.45 (hydrocarbon chain-CH$_2$, 32H), 1.48 (—CO—O—C(CH$_3$)$_3$, 9H), 1.70–1.90 (homocysteine β-CH$_2$,2H), 3.17 (urethane-CH$_2$-hydrocarbon chain 2H), 3.75 (—CO—O—CH$_3$, 3H), 3.30–3.40 (homocysteine γ-CH$_2$, 1H), 4.40–4.75 (homocysteine α-CH$_2$, 2H).

Subsequently, 0.200 g of the Boc-amino ester was dissolved in 5 ml of CH$_2$Cl$_2$. 5 ml of TFA was added thereto, followed by stirring for 30 minutes. Then, the solvent of the resulting solution was distilled away under reduced pressure, followed by drying under reduced pressure. Thus, TFA salt of Compound (5) (represented by Formula (I) wherein R is —O—CH$_3$, R' is —C$_{18}$H$_{37}$, X is —S— and n is 2) was obtained (m.p. 145°–150° C.). This salt was treated with a saturated aqueous solution of NaHCO$_3$. Thus, an amino ester (represented by Formula (I) wherein R is —O—CH$_3$, R' is —C$_{18}$H$_{37}$, X is —S— and n is 2, namely Compound (5)) was obtained as a colorless solid.

EXAMPLE 5

Synthesis of Compound (8) Represented by Formula (I) Wherein R is —O—CH$_3$, R' is —C$_{16}$H$_{33}$, X is —NH— and n is 4

3.65 g (10 millimoles) of N$^\alpha$-Boc-N$^{68}$-Z-lysine was dissolved in 100 ml of THF. After adding 2.06 g (10 millimoles) of dicyclohexylcarbodiimido thereto, the mixture was stirred for 30 minutes. 30 ml of methanol was added and then the mixture was allowed to stand overnight. The precipitate was removed by filtration, and then the solvent of the thus-obtained filtrate was distilled away under reduced pressure. Then, the residue was decomposed with hydrogens generated by adding 150 ml of methanol and palladium carbon (10% content). The reacting solution was filtrated with celite, and then methanol of the filtrate was distilled away under reduced pressure. Thus, 2.1 g (8.1 millimoles) of a Boc-amino ester (represented by Formula (III), wherein R is —O—CH$_3$, X is —NH— and n is 4 ) was obtained.

Then, 2.0 g (10.2 millimoles) of TCF was added dropwise to 2 g of active carbon to produce phosgene, which was introduced into 50 ml of xylene in a three-neck flask under ice cooling. Thereto was added dropwise a solution of 1.2 g (5.0 millimoles) cethylamine in 25 ml of xylene. After heating the mixture, the infrared absorption of 2270 cm$^{-1}$ (C=N=O) was comfirmed.

Xylene in the mixture was thereafter distilled away. 50 ml of THF was added to the residue. 1.3 g (5.0 millimoles) of the previous obtained amino ester (represented by Formula (III), wherein R is —O—CH₃, X is —NH— and n is 4) and 0.500 g (5.0 millimoles) of triethylamine in 50 ml of THF was added thereto. The mixture was allowed to stand overnight. CHCl₃ was added thereto, and then the organic layer was washed with water, followed by Na₂SO₄ drying. CHCl₃ was thereafter distilled away under reduced pressure. The residue was purified by silica gel chromatography (eluent: hexane/ethyl acetate=6/4). Thus, 1.8 g (2.6 millimoles) of an amino ester (represented by Formula (IV) wherein R is —O—CH₃, R' is —C₁₆H₃₃, X is —NH— and n is 4) was obtained. (m.p. 116°-126° C.; ¹H-NMR (CDCl₃, δ) 0.90 (hydrocarbon-chain CH₃, 3H), 1.10-1.45 (hydrocarbon-chain CH₂, 28H), 1.48 (—CO—O—C(CH₃)₃, 9H), 1.70-2.00 (resine β, γ, δ-CH₂, 6H), 3.18 (urethane-CH₂-hydrocarbon-chain, resine ε-CH₂, 4H), 3.75 (—CO—OCH₃, 3H), 4.09 (resine α-CH₂, 1H).

Subsequently, 0.200 g of the Boc-amino ester was dissolved in 5 ml of CH₂Cl₂, and then 5 ml of TFA was added thereto. The reaction of the mixture was conducted for 30 minutes. Then, the solvent of the resulting solution was distilled away under ice-cooling reduced pressure, followed by drying. Thus, TFA salt of compound (8) (represented by Formula (I) wherein R is —O—CH₃, R' is —C₁₆H₃₃, X is —NH— and n is 4) was obtained (m.p. 175°-180° C.). This salt was treated with a saturated aqueous solution of NaHCO₃. Thus, an amino ester (represented by Formula (I) wherein R is —O—CH₃, R is —C₁₆H₃₃, X is —NH— and n is 4, namely Compound (8)) was obtained as a colorless solid.

The amino acid derivatives each having various eliminative groups in the present invention can be synthesized by simple steps using optically active amino acids described above.

While the invention has been described in detailed with reference to specific embodiments, it will be apparent to one skilled in the art that various changes and modifications can be made to the invention without departing from its spirit and scope.

WHAT IS CLAIMED IS:

1. An amino acid derivative represented by the general Formula (I):

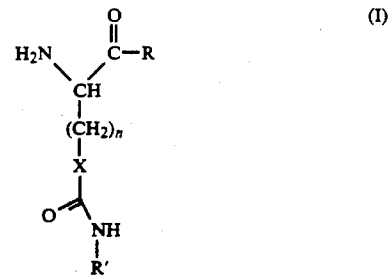

wherein R is a group whose conjugate acid has a pKa ranging from 10 to 16 and R is selected from the group consisting of a phenoxy group, a dichloroethoxy group, a trichloroethoxy group, a monochloroethoxy group, an imidazolyl group, and a

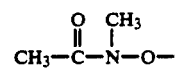

group, R' is a straight chain alkyl group having 12 to 20 carbon atoms, n is an integer of 0 to 4, and X is —O—, —NH— or —S—.

2. The amino acid derivative of claim 1, wherein R' is selected from the group consisting of a dodecyl group, a hexadecyl group, and an octadecyl group.

3. The amino acid derivative of claim 1, wherein R is

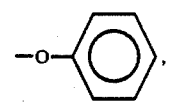

R' is —C₁₈H₃₇, n is 1, and X is —O—.

4. The amino acid derivative of claim 1, wherein R is —O—CH₂CHCl₂, R' is —C₁₈H₃₇, n is 1, and X is —O—.

5. The amino acid derivative of claim 1, wherein n is 1 or 2.

* * * * *